United States Patent [19]

Gaddy et al.

[11] 4,355,108

[45] Oct. 19, 1982

[54] ETHANOL PRODUCTION WITH AN IMMOBILIZED CELL REACTOR

[75] Inventors: James L. Gaddy, Rolla; Oliver C. Sitton, House Springs, both of Mo.

[73] Assignee: The Curators of the University of Missouri, Columbia, Mo.

[21] Appl. No.: 152,365

[22] Filed: May 22, 1980

[51] Int. Cl.$^3$ .................. C12P 7/10; C12N 11/14; C12N 11/06; C12M 1/40

[52] U.S. Cl. ........................... 435/165; 426/11; 435/176; 435/177; 435/288

[58] Field of Search ............... 435/161, 177, 288, 162, 435/176, 174, 165; 426/11, 16

[56] References Cited

U.S. PATENT DOCUMENTS

| | | | |
|---|---|---|---|
| 3,210,196 | 10/1965 | Corran et al. | 426/13 X |
| 3,402,103 | 9/1968 | Amberg et al. | 435/161 X |
| 4,009,286 | 2/1977 | Moll et al. | 426/16 X |
| 4,127,447 | 11/1978 | Griffith et al. | 435/177 X |

OTHER PUBLICATIONS

Griffith et al., A New Method for Coating Tomer Packing so as to Facilitate Microoganism Attachment Developmentation Industrial Microbiology, vol. 17, 1976, pp. 241-246.

Tsao, G. T., Cellulosic Material as a Renewable Resource, Process Biochemistry, 1978 (pp. 12-14).

Converse et al., Acid Hydrolysis of Cellulose in Refuse to Sugars and its Fermentation to Alcohol, Chemical Abstracts, vol. 79: 124663u, 1973, (p. 270).

*Primary Examiner*—David M. Naff

[57] ABSTRACT

Ethanol is produced from cellulosic material such as corn stover by treating the cellulosic material in a first hydrolysis stage with a dilute acid solution to hydrolyze pentosans to xylose, separating solids from the resultant hydrolysate, treating the solids in a second hydrolysis stage with a concentrated acid solution to hydrolyze hexosans to glucose, and fermenting the glucose to ethanol by passing a solution of the glucose over a fixed film of yeast prepared by attaching yeast with a polyfunctional agent to a proteinaceous material coated on a solid support. The use of a first hydrolysis stage avoids the production of furfural which is toxic and inhibits yeast fermentation. Xylose produced from the first stage may also be fermented to ethanol with the fixed film of yeast.

11 Claims, 9 Drawing Figures

PROCESS FOR THE ACID HYDROLYSIS OF CORN RESIDUE

PROCESS FOR THE BIOLOGICAL CONVERSION
OF CORN RESIDUE TO ETHYL ALCOHOL

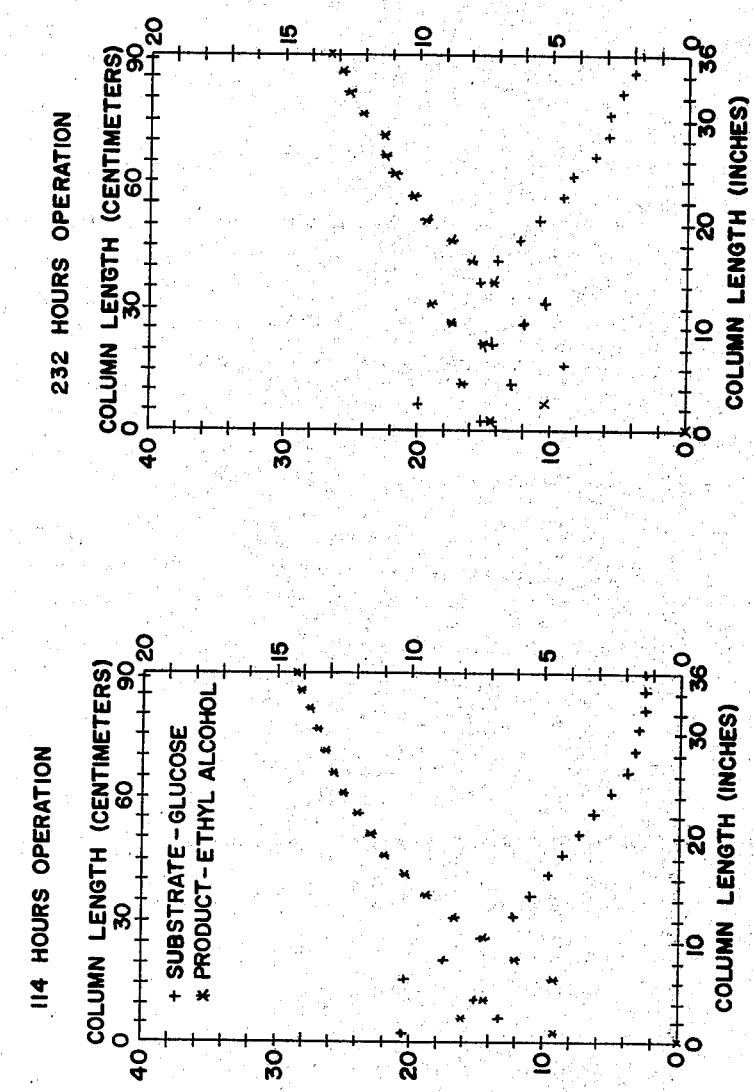
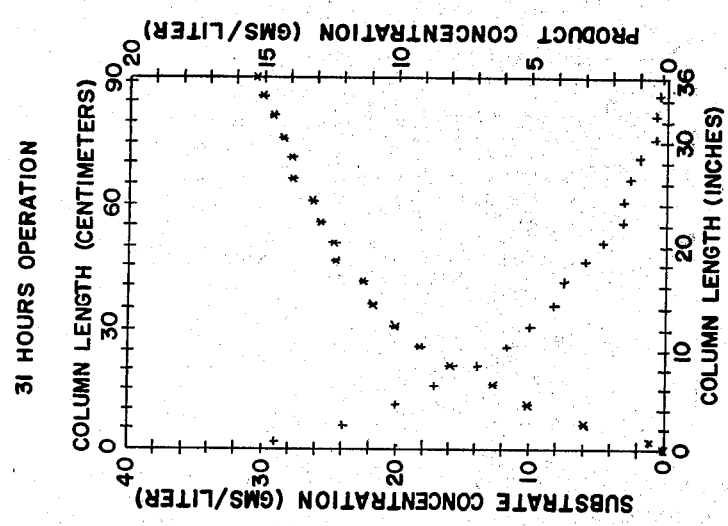

ETHANOL PRODUCTION WITH AN IMMOBILIZED CELL REACTOR

This invention relates to a method of manufacturing ethanol from a sugar substrate and to the immobilized cell reactor useful therefor.

As world reserves of petroleum are depleted, new sources of carbon and hydrogen must be found to supply mankind's chemical and energy needs. In most parts of the world, large quantities of biomass exist which could serve as an energy mechanism or as raw materials for manufacturing chemicals. For example, recent studies indicate that recoverable agricultural residues in the United States alone total 300 million dry tons per year.

In the United States, corn stover is one possible source of biomass. It accounts for about half of the total agricultural residue and about 70 percent of that is produced in the central states so that collection and transportation could be centralized. At present, these corn residues could supply all of the petrochemical needs of the United States with a conversion efficiency as low as 40 percent.

In addition to corn stover, there are many other agricultural residues which can serve as a source of chemicals and energy. Typical other materials are corn cobs, wheat straw, oat hulls, bagasse, pine, oak or the like. While the percentages vary, the primary constituents of all plant materials are hemicellulose, cellulose and lignin. For example, corn stover is 15 percent by weight hemicellulose, 35 percent cellulose and 15 percent lignin. Oat hulls, on the other hand, are 30 percent hemicellulose, 34 percent cellulose and 14 percent lignin.

The hemicellulose and cellulose fractions can be converted into energy or chemicals by direct combustion, pyrolysis or biological conversion. Biological conversion is preferred, however, because of its higher efficiency and the preservation of minerals and nutrients for return to the soil.

In order to bioconvert agricultural residues, however, it is necessary to hydrolyze the hemicellulose and cellulose into monomeric sugars, i.e. pentoses and hexoses, respectively. As is well known, the hydrolysis of hemicellulose and cellulose is catalyzed by enzymes or by mineral acids. The simple sugars can then be converted into alcohols, acids, aldehydes or gases depending on the microorganism selected. While a variety of chemicals can be made from the pentoses and hexoses, the focus of the present invention is on the production of ethanol because of present interest in gasohol and because it is a desirable starting material for chemical synthesis.

Up until now, there have been two ways to convert xylose and/or glucose into ethanol: batch fermentation and continuous stirred tank fermentation. Both of these ways have objectionably slow reaction rates and are quite susceptible to inhibition from materials in the substrate or in the product.

In view of the above, there is a need for a stable, high productivity reactor for converting glucose and/or xylose into ethanol, said simple sugars produced in abundance by hydrolyzing cellulose and hemicellulose containing materials such as corn stover, corn cobs or the like. Therefore among the several objects of the present invention may be noted the provision of a stable, high productivity reactor for converting glucose and/or xylose into ethanol. Other objects and features will be in part apparent and in part pointed out hereinafter.

The invention accordingly comprises the methods and constructions hereinafter described, the scope of the invention being indicated in the subjoined claims.

In the accompanying drawings, in which one of various possible embodiments of the invention is illustrated, corresponding reference numerals refer to corresponding parts and in which:

FIG. 4 shows the performance of an immobilized cell reactor in accordance with the present invention under Test A conditions after 31 hours of operation;

FIG. 5 shows the performance thereof after 114 hours;

FIG. 6 shows the performance thereof after 232 hours;

Figure 1:
FIG. 1 is an electron micrograph (2200×) showing immobilized yeast cells in accordance with the present invention.

In general, the drawings illustrate a process for producing ethanol from a substrate containing a fermentable amount of glucose or xylose wherein the substrate is passed over a fixed film of yeast organisms attached to a proteinaceous coat adsorbed on a solid support. While a particular process for producing ethanol from corn stalks is shown in the drawings, it should be understood that other feed stocks may be used as long as they contain fermentable amounts of xylose or glucose. It should also be understood that while the system illustrated in FIG. 3 ferments both pentoses and hexoses, one or the other may be fermented alone in a single reactor system.

Immobilized cell reactors in accordance with the present invention are prepared by packing a column with an improved packing material with a fixed film of yeast organisms attached thereto. The improved packing material is prepared by coating the packing material with a coat of proteinaceous material, treating the proteinaceous coat with a polyfunctional reagent capable of reacting with at least one amino acid group making up the proteinaceous material, inoculating the treated coat with a yeast organism genetically stable for the production of ethanol and then incubating. It is important that the proteinaceous coat be formed of a polymeric material having reactive groups for reaction with the above mentioned polyfunctional reagent. It is also important that the yeast organisms be genetically stable for the production of ethanol and that the reagent which immobilizes them, not affect their ability to reproduce normally. Suitable organisms for fermenting glucose include *Saccharomyces cerevisiae* and suitable organisms for fermenting xylose include *Fusarium oxysporum* and *Candida utilis*. Other yeasts which occur naturally or may be developed by mutation may also be used as long as they are genetically stable for the production of ethanol, as aforementioned, and can be immobilized, as more particularly described hereinafter.

Suitable reagents reactive with amino acids typically found in film-forming proteinaceous materials include:
dialdehydes such as glutaraldehyde;
diazos such as diazobenzidene-2,2'-disulfonic acid or diazobenzidine-3,3'-dicarboxylic acid;
diisothiocyanates such as 4,4'-diisothiocyanatobiphenyl-2,2'-disulfonic acid;
diisocyanates such as hexamethylenediisocyanate;
dihalos such as 1,5-difluoro-2,4-dinitrobenzene; and,
iodoacetamides such as N,N'-hexylmethylene-bis-iodoacetamide. It is preferred that the proteinaceous coat be gelatin and that the polyfunctional reagent be glutaraldehyde or diisocyanates. Of these, glutaraldehyde is preferred since it reacts faster and also tends to harden the gelatin film which prevents it from being washed away. The solid support is preferably porous or otherwise provided with a large surface area. Porous ceramic solid supports such as Raschig rings are particularly preferred.

The proteinaceous coat and polyfunctional reagent are preferably applied to the packing material and it is used for packing a column in the ordinary manner. This is done before the reaction between the proteinaceous coat and the polyfunctional reagent has gone to completion so that there is some of the reagent left for reaction with the lipoproteins making up the cell walls of the yeast. Since the immobilized cell reactor is best used under plug flow conditions, provision is made for spreading the substrate radially evenly at the inlet and the ratio of the diameter of the packing material to the diameter of the column is preferably in the order of 6 to 10 but other ratios can be used and may, under some circumstances, be preferred. The packed column is then sterilized with ethylene oxide or the like, inoculated with the selected yeast organism and substrate slowly flowed through the column. Since the yeast organisms named above are anaerobic, it is preferred that the substrate be upflowed through the column since it can thus be used to displace the air. The substrate can be downflowed but the flow rate must be more carefully controlled if anaerobic conditions are to be maintained.

With the yeast immobilized, it is possible to get much higher cell densities per packed volume that is possible with a batch reactor or with a continuous stirred tank reactor. It is also possible to operate at dilution rates that exceed the maximum specific growth rate of the microorganism whereas with stirred tank reactors, where the organisms are not immobilized, this would result in washout. The higher cell densities and faster dilution rates produce higher productivities than are possible in the above-mentioned conventional reactors. Immobilizing the yeast also has a beneficial effect on the stability of the system since the thickness of the film buffers upsets in pH and flow rates and mitigates inhibition by toxic materials in the substrate or in the products. This is because the concentration of any material in the bulk liquid drops off as it diffuses into the film. While the outer layer may be inhibited and perhaps even washed away, when the upset passes, the remaining inner layers will reproduce normally.

In an immobilized cell reactor as described above, rapid growth occurs at the interface between the fixed film of organisms and the bulk liquid. This interface is called the active zone. As the substrate diffuses into the film, it is consumed and eventually the concentration drops to zero. Since the growth rate is a function of substrate concentration and since the bulk substrate concentration changes within the reactor as a function of distance from the inlet as it is consumed, the thickness of the active zone and the thickness of the film vary with distance from the inlet, starting as thicker at the bottom and becoming thinner towards the top.

As the film grows, the void volume in that portion of the column decreases and there is no longer plug flow. Since the flow rate of the substrate does not change, its velocity through the plugged portion of the column increases and the conversion rate drops. At some point the overall productivity of the column drops to such a level that it is necessary to regenerate the column. This can be accomplished by sparging the overgrowth with a charge of compressed gas which is essentially non-toxic to the yeast organisms such as nitrogen, carbon dioxide or the like. Moderate pressures are used up to the pressure that the outside wall of the reactor can withstand. By so sparging the overgrowth, the productivity of the reactor is returned to its formerly high levels and continuous fermentation is begun again.

Figure 2:
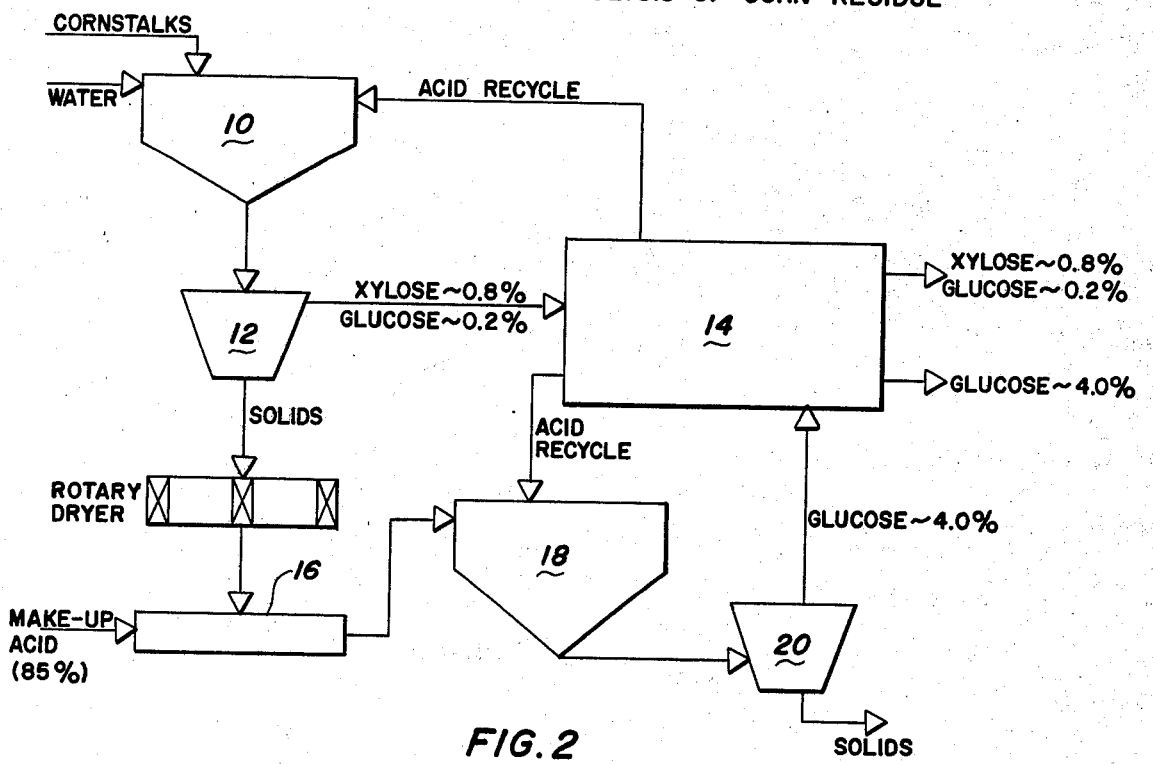
FIG. 2 is a diagrammatic view of a typical two-step process for acid hydrolysis of corn stalks into a prehydrolyzate fraction which is rich in xylose and a hydrolyzate fraction which is rich in glucose.

Referring to the drawings more particularly by reference character, FIG. 2 shows a two-step process for hydrolyzing corn stover and other agricultural residues containing significant amounts of cellulose and hemicellulose. In this process, the pentosans are extracted first in a dilute acid step as xylose and the hexosans are then extracted in a more concentrated acid step as glucose. The use of a prehydrolysis step allows removal of the xylose and avoids contacting it with the more concentrated acid which is necessary to extract the pentosans thus avoiding degradation of it into furfural which is toxic and if not removed would inhibit fermentation. The two-step process produces separate sugar solutions which are desirable because different organisms are required for efficient conversion of glucose and xylose into ethanol and whereas agricultural residues contain significant amounts of pentosans as well as hexosans, both must be utilized for an economic process.

As shown in FIG. 2, ground corn stover is reacted in a prehydrolysis tank 10 with a dilute mineral acid for such time as to hydrolyze the pentosans to xylose. During the prehydrolysis step some of the hexosans are also hydrolyzed but most are not. Suitable prehydrolysis conditions are provided with 4.4 percent sulfuric acid at 100 degrees C. for 50 minutes. The mixture is then passed through a separator 12 such as a filter or a centrifuge. The filtrate comprises about 0.80 percent xylose and about 0.20 percent glucose and is processed through an acid recovery unit 14 such as a dialysis unit where the acid is recovered for recycle. The resultant effluent from the acid recovery unit makes up the prehydrolyzate or first-stage hydrolyzate.

The solids recovered at separator 12 are dried and treated in an impregnator 16 with concentrated mineral acid. This mixture is then fed into a second hydrolysis tank 18 where it is refluxed for such time as to hydrolyze the hexosans to glucose. For this purpose, it has been found effective to mix the dried solids with 85 percent sulfuric acid, to which dilution water is then added such that the concentration of the sulfuric acid is diluted to 8 percent, followed by reacting at 110 degrees C. for 10 minutes. The mixture is then passed through a second separator 20 such as a filter or a centrifuge. This filtrate comprises about 4.0 percent glucose and, like the first filtrate, is processed through acid recovery unit 14.

The effluent from the acid recovery unit makes up the hydrolyzate or second-stage hydrolyzate.

Figure 3:
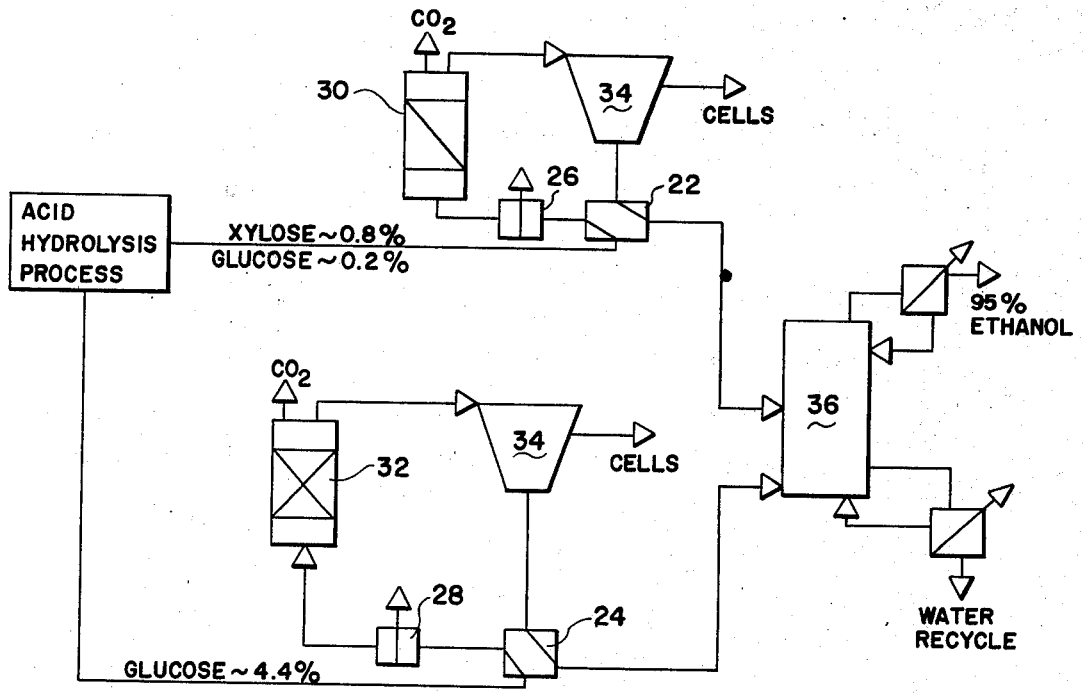
FIG. 3 is a diagrammatic view of a process for converting the prehydrolyzate fraction and hydrolyzate fraction into ethanol in first and second immobilized cell reactors making use of immobilized yeast cells like those shown in FIG. 1.

As shown in FIG. 3, the prehydrolyzate and hydrolyzate produced as shown in FIG. 2 are cooled by heat exchange at 22 and 24 with the reactor effluent streams. They are further cooled in heat exchangers 26 and 28 to the optimal temperature required by the organisms for growth and are then converted, after essential vitamins and other nutrients have been added, into ethanol in first and second immobilized cell reactors 30 and 32, respectively. The cells are harvested at 34 by centrifugation or the like and the ethanol is separated by distillation at 36. The cells are stored for several days during which autolysis occurs. Essential minerals and media supplements can be added to the vitamin rich lysed cells and mixed with the incoming media or the cells can simply be returned to the soil along with the lignin collected at separator 20.

The following examples illustrate the invention and are based on a thesis by O. C. Sitton entitled *The Biological Conversion of Corn Residue into Ethyl Alcohol Using an Immobilized-Cell Reactor* at the University of Missouri-Rolla in 1979 which is incorporated by reference herein as further illustrating the invention.

EXAMPLE 1

For purposes of comparison with the immobilized cell reactor described in Example 2, a 3 percent synthetic media was fermented with *Saccharomyces cerevisiae* in a New Brunswich Model C 30 chemostat continuous stirred-tank reactor. The organisms used for this example were freeze-dried cultures from the American Type Culture Collection, ATCC 24858. Isolated colonies from a streak plate were cultured and maintained as a stock culture. General aseptic conditions were used in handling the culture, media and samples in this and the following example.

The chemostat was sterilized by autoclaving the system at 121 degrees C. for 45 minutes. After cooling overnight, the system was flushed with three reactor volumes of sterile media consisting of 30 g/l glucose, 8.5 g/l yeast extract, 1.3 g/l ammonium chloride, 0.1 g/l magnesium sulfate, 0.1 g/l calcium chloride and 0.1 g/l potassium phosphate. The chemostat was allowed to stand overnight, then observed for contaminant growth and, if not sterile, the procedure was repeated.

When sterile, 10 ml of a 12 hour old culture of *Saccharomyces cerevisiae* was added to an inoculant. The culture was allowed to grow for 4 hours before the test flow rate was started. The pH was controlled at 4.1 by addition of ammonium hydroxide or sulfuric acid. Five retention periods were allowed to elapse between test flow rates to establish steady state. The liquid was then sampled at intervals of one retention period until there was no significant change between three successive samples.

Glucose conversion was 100 percent at a dilution rate of 0.04/hour, indicating that sufficient nutrients were available. Over the range of dilution rates from 0.04/hour to 0.28/hour, the product and cell concentrations were maximum at 13.5 g/l and 3.1 g/l respectively at a dilution rate of 0.04/hour. Increasing the dilution rate decreased the cell concentration and consequently decreased substrate conversion levels.

Washout conditions occurred at a dilution rate of 0.28/hour. Maximum ethanol productivity was 1.75 g/l-hour occurring at a dilution rate of 0.18/hour. Product yields were 0.45 g of product per gram of glucose converted at a dilution rate of 0.04/hour and decreased to 0.30 g/g near washout conditions. Cell yields were 0.1 g of cells per gram of glucose converted.

When second-stage corn stalk hydrolyzate was substituted for the glucose in the synthetic media and the glucose concentration adjusted to 3 percent for comparison, glucose conversion dropped to 97 percent at a dilution rate of 0.04/hour. Maximum product and cell concentrations were 9.4 g/l and 2.9 g/l respectively at a dilution rate of 0.04/hour. As with the synthetic media, increasing the dilution rate decreased the cell concentration with consequent decreases in glucose conversion. However, with second-stage hydrolyzate, cell washout occurred at 0.22/hour which was considerably less than 0.28/hour with the synthetic media. Maximum ethanol productivity was 1.0 g/l-hour at a dilution rate of 0.12/hour. Product yield was 0.32 g/g and cell yield was 0.1 g/g.

EXAMPLE 2

An immobilized cell reactor in accordance with the present invention was constructed from a 107.0 cm long by 6.35 cm diameter OD flanged plexiglass tube with 0.64 cm thick walls. Two circular plexiglass plates were cut to fit over the ends of the tube and were machined at the center for a 0.32 cm by 0.16 cm NPT Swagelok male connector. Joint gaskets were made of Teflon and were used to seal the end plates to the tube flanges. The reactor wall was machined on 5.08 cm axial centers for 0.32 cm by 0.16 cm NPT Swagelok male connectors which served as sample ports. Four thermocouples were positioned equidistant along the reactor length to measure the bulk liquid temperature profile.

The liquid feed media flowed from a feed reservoir which was located 45.6 cm above the reactor through a feed pump and into the bottom plate of the reactor. Two perforated plates in the reactor inlet radially distributed the incoming media. Spacers separated the plates by 0.32 cm and held the plates so that the hole patterns were offset by 90 degrees. Media flowed vertically up through the column. Gaseous products were discharged through the reactor top to a Precision Scientific wet test meter which measured the flow rate.

Ceramic Raschig rings, 0.64 cm nominal size randomly filled the column to a packing height of 91.5 cm. The tube diameter to nominal packing diameter ratio was 8 to minimize wall effects. The total reactor volume was 1853 ml and the void volume was 902 ml.

Before the Raschig rings were packed in the column, they were sterilized and dip-coated in a sterile 25 percent gelatin solution. The coated rings were then sprayed with 3 percent glutaraldehyde and dried for 24 hours. The reactor was then randomly packed and the reactor closed and sterilized by passing ethylene oxide through it for 10 minutes. An inoculating culture of *Saccharomyces cerevisiae* like that in Example 1 was then pumped into the reactor and allowed to stand for 4 hours. Air was displaced from the reactor by the liquid and any dissolved oxygen was readily consumed by the initial culture. Media was pumped at a low flow rate for 4 more hours and then the test flow rate was started. Glucose and ethanol concentration profiles were determined by analyzing bulk liquid samples taken from the sample ports at each test flow rate. Several profiles were measured for each flow rate. Initially, the profiles were measured every two days but in later tests longer times were allowed to elapse between measurements.

Table I lists the conditions for the immobilized cell reactor tests. In each such test, with the exception of E and F, the media included nutrients in the same amounts as in Example 1. In tests E and G, the amount of nutrients was halved. As indicated in Table I, media flow rate, glucose concentration and glucose source were varied. The pH of autoclaved synthetic media was 4.1 and since there was negligible pH adjustments needed in the stirred reactor tests described in Example 1, the pH was not controlled in this example. The effluent pH was measured periodically and did not vary from 4.1. The pH of the media containing second-stage corn stalk hydrolyzate from was adjusted to 4.1 by lime addition. The column was operated at room temperature and at atmospheric pressure. Temperature variations along the length of the column were less than 0.2 degrees C. and the liquid pressure drop was less than 12 inches of water. Concentration profiles were measured at different times during each test.

TABLE I

| Group | Media Source | Glucose Concentration g/l | Flow Rate ml/hour |
| --- | --- | --- | --- |
| A | Synthetic | 30 | 250 |
| B | Synthetic | 30 | 500 |
| C | Synthetic | 30 | 125 |
| D | Synthetic | 60 | 250 |
| E | Synthetic (half nutrients) | 30 | 250 |
| F | Hydrolyzate | 30 | 250 |
| G | Hydrolyzate (half nutrients) | 30 | 250 |

FIGS. 4 through 9 show the substrate and product concentration profiles for group A test conditions (synthetic media, 30 g/l and 250 ml/hour). FIG. 4 shows the concentration profile after 31 hours of operation. Conversion of glucose was 99.4 percent with product yield at 0.5 g/g. Glucose concentration decreased more rapidly at the inlet than at the exit of the column. FIG. 5 shows the concentration profiles after 114 hours of operation. At this time a cellular film was visible on the packing material in the column and appeared most dense at the column inlet. The data scatter in the measured concentration in the first 4.5 inches of the column indicated that the media flow was channelling in this section. The reduced void volume decreased glucose conversion to 91.2 percent.

Figure 7:
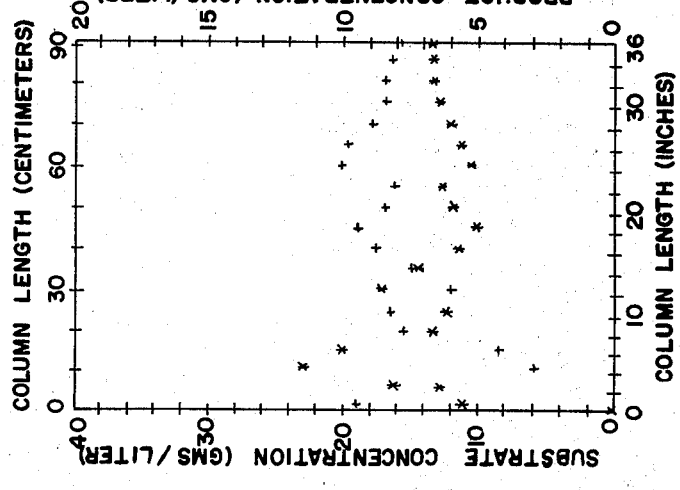
FIG. 7 shows the performance thereof after 334 hours.

FIG. 6 shows the profile after 232 hours of operation. The degree of channelling had increased and could be seen in the inlet section of the column. FIG. 7 shows the profiles after 334 hours of operation. Channelling conditions existed in 63 percent of the column volume. Glucose conversion decreased to 48.0 percent. Clearly, the cell overgrowth was decreasing reactor performance. The column was drained and the liquid volume was 120 ml which was an 88.0 percent decrease from initial start-up. For continued operation, the cell overgrowth had to be removed.

Figure 9:
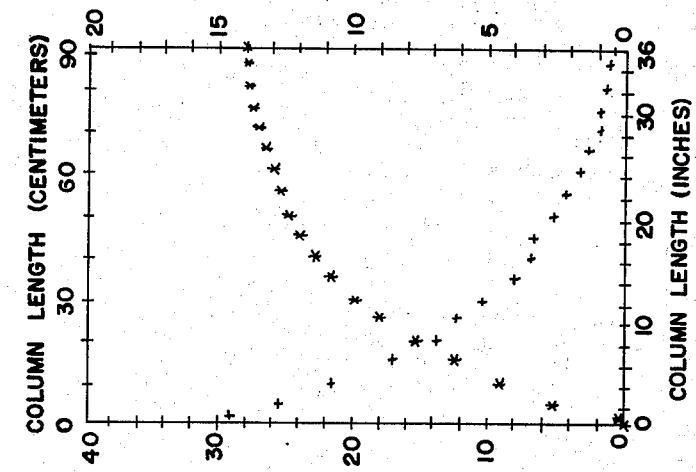
FIG. 9 shows the performance thereof after a second regeneration.
Figure 8:
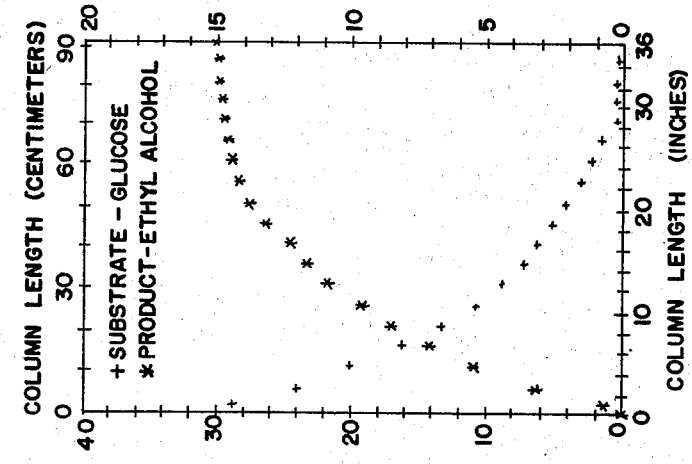
FIG. 8 shows the performance thereof after a first regeneration.

Liquid flow rates as high as 100 ml/minute did not remove the overgrowth from the void spaces. However, flowing nitrogen gas through the packed bed at flooding conditions for 10 minutes removed 58.9 g of cells from the packing material. Nitrogen gas pressure was 30 psig. FIG. 8 shows the concentration profiles 4 hours after regeneration. Glucose conversion increased to 99.9 percent. The column was drained again and the liquid volume was 580 ml. Twenty-nine hours after regeneration, glucose conversion had decreased to 95.2 percent. Cell overgrowth and consequently flow channelling were evident again. Therefore commercial operation of this type of reactor would require repeated regenerations. FIG. 9 shows the concentration profiles 4 hours after the second regeneration whereupon glucose conversion was returned to 98.7 percent. The liquid volume was 615 ml and cell yield on regeneration was 6.2 g.

Under test B conditions (synthetic media, 30 g/l and 500 ml/hour), glucose conversion was 88.2 percent after 31 hours of operation. Product yield was 0.5 g/g. After 155 hours of operation, channelling was evident in 50 percent of the column and glucose conversion was reduced to 61.2 percent. After regeneration, the liquid volumes were 655 and 690 ml respectively. Glucose conversions were 86.2 and 90.0 percent. Cell yield on regeneration was 4.9 g.

Under test C conditions (synthetic media, 30 g/l and 125 ml/hour), glucose conversion was essentially 100 percent even after 75 hours of operation. Channelling was not evident. After regeneration, glucose conversion was again essentially 100 percent. Liquid volume was 495 ml and 525 ml respectively. Product yield was 0.5 g/g. Cell yield on regeneration was 3.4 g.

With test D conditions (synthetic media, 60 g/l and 250 ml/hour), glucose conversion was 99.7 percent with a 0.43 g/g product yield after 14 hours. After 105 hours, glucose conversion had decreased to 93.6 percent. After the first and second regenerations, glucose conversions were 98.3 and 98.6 percent respectively. Liquid volumes were 515 and 535 ml. Cell yield was 42.4 g.

For test E conditions (synthetic media, 30 g/l, half nutrients and 250 ml/hour), glucose conversion was only 80.0 percent with a product yield of 0.5 g/g after 51 hours of operation. After 116 hours, glucose conversion had dropped even further to 79.1 percent with channelling occurring to 10 percent of the column volume. Glucose conversion after regeneration was 85.2 and 86.2 percent with liquid volume at 450 and 490 ml, respectively. These results show that reactor performance is reduced when the nutrients were supplied below the optimal original levels.

Test F measured the profiles for hydrolyzate feed material. In this case, glucose conversion was 93.7 percent afer 62 hours of operation. Product yield was 0.5 g/g. After regeneration, the cell yield was 10.7 g and the liquid volume was 550 ml.

Test G measured the profiles for hydrolyzate but with half nutrients. The effect was to reduce glucose production to 81.9 percent after only 64 hours of operation.

In general the immobilized cell reactor described in tests A through G was very stable and easily regenerated. It withstood periods as long as 48 hours without feed material and restarted once flow began. At one time a contaminant entered the system as detected by extraneous peaks in the chromatographic analysis of the effluent. However, after two days and one regeneration the contaminant disappeared. Dilution rates as high as 1.75/ hour were attained in group B tests without upset in reactor operation. This value is almost 6 times the washout rate measured in the chemostat in Example 1 and indicates that cross-linking Saccharomyces cerevisiae to a gelatin coated support with glutaraldehdye is an effective method of immobilization. Consequently, the ethanol productivity based on liquid volume was 15.9 g/l-hour which is 9 times the maximum productivity measured in the chemostat. There was no apparent effect on the immobilized cell reactor performance when ethanol concentrations exceeded 12 g/l, and there was not as great a change in performance when hydrolyzate was used as feed material. The product yield maintained steady at 0.5 g/g in the immobilized cell reactor described in Example 2, whereas the yield varied from 0.5 to 0.3 g/g in the chemostat described in Example 1.

In view of the above, it will be seen that the several objects of the invention are achieved and other advantageous results attained. As various changes could be made in the above constructions and methods without departing from the scope of the invention, it is intended that all matter contained in the above description or shown in the accompanying drawings shall be interpreted as illustrative and not in a limiting sense.

What is claimed is:

1. A process for producing ethanol from cellulosic material containing pentosans and hexosans comprising treating the cellulosic material in a first hydrolysis stage with a dilute acid solution to hydrolyze the pentosans to xylose without substantial hydrolysis of hexosans to glucose, separating solids from the resultant hydrolyzate, treating the solids in a second hydrolysis stage with a concentrated acid solution to hydrolyze the hexosans to glucose, and fermenting the glucose to ethanol by passing a solution of the glucose over a fixed film of yeast organisms which ferment said glucose to ethanol, said film of organisms being prepared by coating a solid support with proteinaceous material having free amino groups, treating the proteinaceous material with a polyfunctional agent which is capable of reacting with free amino groups and inoculating the treated proteinaceous material with an inoculum of the yeast organisms, said yeast organisms having free amino groups and said polyfunctional agent reacting with free amino groups contained by the proteinaceous material and the yeast organisms said inoculum being added from solution before the reaction between the polyfunctional agent and the proteinaceous material has substantially gone to completion whereby the yeast organisms are attached to the proteinaceous coat by the polyfunctional agent such that a substantial number of bonds are formed between the yeast and the proteinaceous coat.

2. The process of claim 1 wherein the proteinaceous coat is gelatin.

3. The process of claim 2 wherein the polyfunctional reagent is a bifunctional member selected from the group consisting of glutaraldehyde and diioscyanates.

4. The process of claim 2 wherein the polyfunctional reagent is glutaraldehyde.

5. The process of claim 4 wherein the fixed film of organisms are sparged with compressed gas to remove cell overgrowth.

6. The process of claim 5 wherein the organisms are sparged with compressed nitrogen.

7. The process of claim 4 wherein the yeast is *Saccharomyces cerevisiae*.

8. The process of claim 7 wherein the solid support is a porous ceramic support.

9. The process of claim 1 wherein the xylose from said first hydrolysis stage is fermented to ethanol with a film of yeast organisms prepared according to claim 1.

10. A process for producing ethanol from corn stover containing pentosans and hexosans comprising treating the corn stover in a first hydrolysis stage with a dilute acid solution to hydrolyze the pentosans to xylose without substantial hydrolysis of hexosans to glucose, separating solids from the resultant hydrolyzate, treating the solids in a second hydrolysis stage with a concentrated acid solution to hydrolyze the hexosans to glucose, and fermenting the glucose to ethanol by passing a solution of the glucose over a fixed film of *Saccharomyces cerevisiae* which ferment said glucose to ethanol, said film of *Saccharomyces cerevisiae* being prepared by coating a porous ceramic support with gelatin having free amino groups, treating the gelatin coat with glutaraldehyde which is capable of reacting with free amino groups and inoculating the treated gelatin coat with an inoculum of *Saccharomyces cerevisiae*, said yeast organisms having free amino groups and said glutaraldehyde reacting with the free amino groups in the gelatin coat and in the *Saccharomyces cerevisiae*, sad inoculum being added from solution to the treated gelatin coat before the reaction between the glutaraldehyde and the gelatin coat has substantially gone to completion whereby the *Saccharomyces cerevisiae* are attached to the gelatin coat by the glutaraldehyde such that a substantial number of bonds are formed between the *Saccharomyces cerevisiae* and the gelatin coat.

11. The process of claim 10 wherein the xylose from said first hydrolysis stage is fermented to ethanol with a film of yeast organisms prepared according to claim 10.

* * * * *